United States Patent [19]

Datta et al.

[11] Patent Number: 4,560,658
[45] Date of Patent: Dec. 24, 1985

[54] PRODUCTION OF BUTANOL BY FERMENTATION IN THE PRESENCE OF CARBON MONOXIDE

[75] Inventors: Rathin Datta, Chicago, Ill.; Joseph G. Zeikus, Okemos, Mich.

[73] Assignee: CPC International Inc., Englewood Cliffs, N.J.

[21] Appl. No.: 558,149

[22] Filed: Dec. 5, 1983

[51] Int. Cl.$^4$ .................... C12P 7/16; C12R 1/145
[52] U.S. Cl. ............................... 435/160; 435/842
[58] Field of Search ............... 435/41, 150, 155, 160, 435/141, 813, 842

[56] References Cited

U.S. PATENT DOCUMENTS 1,315,585  9/1919  Weizmann.

OTHER PUBLICATIONS

Casida, L., Industrial Microbiology, 1968, pp. 258–274.
Wiseman, A., Topics in Enzyme and Fermentation Biotechnology, 7, p. 173, 1983.
The Condensed Chemical Dictionary, p. 197, (Van Nostrand, Rheinhold Co., (1983)).
Simon, E. and Weizmann, C., *Enzymologia*, 4, 169–188 (1937).
Simon, E., *Arch. Biochem.*, 13, 237–243 (1947).

Primary Examiner—Thomas G. Wiseman
Assistant Examiner—Jean A. Heck
Attorney, Agent, or Firm—Stanley M. Parmerter

[57] ABSTRACT

An improved process for the production of butanol by fermentation of carbon-containing compounds with *C. acetobutylicum* is disclosed. The fermentation is conducted in an aqueous medium containing a sufficient concentration of dissolved carbon monoxide to give increased yields of butanol while suppressing the formation of hydrogen and acetone. This fermentation also gives increased conversion of butyric acid to solvents.

12 Claims, No Drawings

PRODUCTION OF BUTANOL BY FERMENTATION IN THE PRESENCE OF CARBON MONOXIDE

FIELD OF THE INVENTION

This invention relates to an improved method for the production of butanol and smaller amounts of other solvents by a fermentation process conducted in the presence of carbon monoxide.

BACKGROUND OF THE INVENTION

The fermentation of carbohydrates to form butanol and acetone by *Clostridium acetobutylicum* (hereafter abbreviated *C. acetobutylicum*) was disclosed by Weizmann in U.S. Pat. No. 1,315,585. For many years, this process was used for the preparation of acetone and butanol, and a certain amount of ethyl alcohol was obtained as a by-product.

Eventually, the microbial process was displaced by chemical processes which provide the same products using cheap fossil fuel raw materials. However, the gradual depletion of petroleum fossil fuel with the resultant increase in prices of petrochemical feedstocks has revived interest in the fermentation reaction that uses carbohydrates, which are renewable raw materials.

The earlier commercial production of butanol by the fermentaion process gave relatively large amounts of the less-valuable solvent, acetone, as a by-product. In addition, large volumes of hydrogen gas were evolved. The formation of these by-products uses up carbohydrate which could be otherwise converted to the more-valuable butanol. It would, therefore, be an improvement in the process if some means could be provided to reduce the formation of the by-products, acetone and hydrogen, and to increase the yield of butanol.

In 1937, Simon and Weizmann reported an attempt to modify the fermentation by *C. acetobutylicum* with carbon monoxide, *Enzymologia*, 4. 169–188 (1937). They reported there was no change in the fermentation of a 5% suspension of corn mash when a slow stream of carbon monoxide was passed through the fermentation medium. Simon later reported, *Arch. Biochem.*, 13, 237–243 (1947), that this failure to influence the fermentation with a 5% corn mash is apparently due to mechanical factors. When the fermentation is run with a more dilute mash or in the presence of simpler sugars, it is almost completely inhibited when a stream of carbon monoxide is passed through the medium. Simon also isolated bacterial cells from a 24-hour fermentation and found that they would ferment glucose in an atmosphere of carbon monoxide. Under these conditions, the product was exclusively racemic lactic acid.

We have now discovered, surprisingly that if carbon monoxide is diluted sufficiently it exhibits an entirely different influence on the course of the fermentation of carbohydrates by *C acetobutylicum*. When the fermentation is run in the presence of properly diluted carbon monoxide, the formation of acetone and hydrogen is reduced and the production of butanol is increased. Furthermore, if the fermentation is carried out in the presence of butyric acid, the carbon monoxide greatly enhances its conversion to butyl alcohol.

SUMMARY OF THE INVENTION

In accordance with this invention, there is provided an improved process for the preparation of butanol by the fermentation of carbon-containing compounds by *C. acetobutylicum*. This improved process comprises conducting the fermentation in an aqueous medium containing a sufficient concentration of dissolved carbon monoxide to give increased yields of butanol over those obtained in the absence of carbon monoxide and decreased yields of hydrogen and acetone over those obtained in the absence of carbon monoxide.

Further, in accordance with this invention, there is provided a process for the preparation of butanol by the fermentation of carbon-containing compounds comprising butyric acid by *Clostridium acetobutylicum* wherein the improvement comprises conducting the fermentation in the presence of an aqueous medium containing a sufficient concentration of dissolved carbon monoxide to give an increased conversion of butyric acid to solvents over the conversion obtained in the absence of carbon monoxide.

DETAILED DESCRIPTION OF THE INVENTION

The fermentation process of this invention involves the fermentation of carbohydrates by a strain of *C. acetobutylicum* to form butanol and lesser amounts of other materials. In general, any strain of *C. acetobutylicum* which forms primarily butanol can be employed. A useful strain for the practice of this invention is the strain of *C. acetobutylicum*, ATCC 4259, which is available from the American Type Culture Collection, Rockville, Md. A preferred strain for the use of this invention is the asporogenic strain of *C. acetobutylicum*, ATCC 39236, which is described in detail in a copending U.S. patent application, Ser. No. 442,805, titled "Improved Strain of *Clostridium acetobutylicum* and Process for Its Preparation", now U.S. Pat. No. 4,521,516.

The carbohydrate used in the practice of this invention can be any carbohydrate that is fermented by the strain of *C. acetobutylicum* used. These carbohydrate sources include solubilized starches and sugar syrups, as well as glucose or sucrose in pure or crude forms. The fermentation medium should also contain nutrients and other growth factors needed for growth and reproduction of the microorganism employed.

When the strains of *C. acetobutylicum* are ATCC 4259 or ATCC 39236, a suitable medium for carrying out the fermentation process of this invention comprises an aqueous solution of a low D.E. (dextrose equivalent) starch hydrolyzate to which has been added a small amount (from about 0.5% to about 2% by weight, dry basis) of corn steep liquor. Small amounts of corn gluten can also be added to the fermentation. Low D.E. (about 5 D.E. to about 20 D.E.) starch hydrolyzates produced by the partial hydrolysis of starch, are readily available from the corn milling industry. Likewise, corn steep liquor, which is produced when corn is steeped in a dilute solution of sulfur dioxide, is available from the corn wet-milling industry.

The fermentation process of the present invention is initiated by introducing cells of a strain of *C. acetobutylicum* into a sterile medium in an inoculum-producing reactor. Fermentation is allowed to continue until a good growth of cells is developed. These cells can be used to inoculate the fermentation used for solvent production. Alternatively, these cells can be used to inoculate a continuous culture run in a chemostat operated as a continuous inoculum-producing reactor. The continuous inoculum-producing reactor is run at a dilution rate which prevents the buildup of solvents in the medium and produces vigorous healthy cells of the culture with little exposure to butanol. This is accomplished by a proper selection of dilution rate. In the description of such a reactor, the words "dilution rate" designate the value obtained by dividing the flow rate of the medium through the reactor in volume units per hour by the operating volume of the reactor measured in the same volume units. It has the dimensions of per hour.

Inoculum formation and solvent production are carried out at a temperature of from about 34° C. to about 40° C. and at a pH of from about 4.5 to about 6.5. The reactions are run under anaerobic conditions using medium which has been sterilized by heat or other means well known in the fermentation art.

The carbon monoxide used in the process of this invention need not be pure but should not contain impurities which react with or inhibit the fermentation by *C. acetobutylicum*. The carbon monoxide used in the process of this invention is diluted with other gases such as nitrogen, hydrogen and carbon dioxide, which do not react with or inhibit the fermentation by *C. acetobutylicum*. A convenient gas used for the dilution of carbon monoxide is the commercially available anaerobic gas mixture which contains approximately 90% nitrogen, 5% hydrogen and 5% carbon dioxide, available from the Mathaeson Company, Joliet, Ill.

In the practice of this invention, the fermentation is carried out in an aqueous medium in equilibrium with a gas containing carbon monoxide at a partial pressure of from about 0.05 atm to about 0.3 atm. Although lower partial pressures of carbon monoxide can be used, they exert less influence on the products of the fermentation. Higher partial pressures of carbon monoxide can also be employed, but they inhibit the fermentation process and the growth of cells to such an extent that they are not useful. The preferred partial pressure of carbon monoxide in the gas used in the process of this invention, is from about 0.1 atm to 0.2 atm.

In practicing the carbon monoxide modulated fermentations of this invention, the fermentations can be carried out in any manner such that the carbon monoxide-containing gas is in intimate contact with the fermentation medium. This can be achieved by sparging the fermentation medium with the carbon monoxide-containing gas or by stirring the medium in a closed container which contains the gas of desired concentration in the headspace of the container. Other methods of gas liquid contact which are routinely practiced in biochemical processing and which are familiar to practitioners in the field can be used.

An unexpected benefit of the carbon monoxide modulated fermentation of this invention is the discovery that it gives increased conversion of butyric acid to solvents. This is observed when butyric acid is used as part of the carbon-containing material in the fermentation medium. This finding is important since butyric acid is available as a by-product of other fermentation reactions.

The following examples further describe the embodiments of this invention. All parts are by weight and all percentages are by weight unless expressly stated to be otherwise.

Solvent concentrations were determined using high-performance liquid chromatography (HPLC). Components were analyzed chromatographically by elution with 0.006N $H_2SO_4$ from a cation-exchange resin in the hydrogen form. The eluted components were detected by means of a differential refractometer, plotted on a recorder and quantitated using an electronic integrator. The area under the curve, which represents the concentration of each component, is reported as a percentage of the total area. The general procedure is that given in "Analysis of Carbohydrate Mixtures by Liquid Chromatography", *Am. Soc. Brew. Chem. Proc.*, 1973, pp. 43–46. The separations were made on a 1-foot HPX-87 column in the hydrogen form, available from Bio-Rad Laboratories, Richmond, Calif.

EXAMPLE 1

A culture of *C. acetobutylicum*, ATCC 39236, available from the American Type Culture Collection, Rockville, Md., was used in this example. Seed culture for initiating a continuous culture was developed in a 125-ml Erlenmeyer seed flask containing 100 ml of an aqueous medium consisting of 10% by weight dry basis of a 10 D.E. starch hydrolyzate (available from the Grain Processing Company, Muscatine, Iowa, as Maltrin M-100), and 1% by weight dry basis of corn steep liquor (available from the Corn Products Unit of CPC International Inc., Englewood Cliffs, N.J., as Code E801). The pH of the medium was adjusted to 6 2 with concentrated $NH_4OH$ solution before it was sterilized by heating in an autoclave at 121° C. for 20 minutes. The cool sterile medium in a seed flask was inoculated with 5 ml of a suspension of cells of the culture contained in the same medium. The seed flask with inoculated medium was incubated in an anaerobic chamber for 21 hours at 35° C.

Seed culture (75 ml) from the seed flask was used to inoculate a continuous fermentation conducted under anaerobic conditions in a standard 2-liter New Brunswick Bioflow, Model C-30 chemostat containing a bottom-driven magnetic stirrer. The aqueous medium used for the fermentation contained 6% by weight dry basis of 10 D.E. starch hydrolyzate and 0.75% by weight dry basis corn steep liquor adjusted to a pH of 5.0–5.1 with 4N NaOH. The operating volume was 725 ml. The fermentor was first filled with growth medium sparged with anaerobic grade $CO_2$ for 30 minutes before it was adjusted to a pH of 6.1 to 6.2 with concentrated ammonium hydroxide. The mixture was then inoculated with the seed culture and stirred at a rate of 200 revolutions per minute at 37° C. for 4 hours before medium flow in and out of the fermentor was begun. The seed culture chemostat was maintained at a dilution rate of 0.25 $hr^{-1}$. When the cells in the continuous fermentor were growing rapidly at the acidogenic stage of the fermentation, they were used to inoculate the fermentation of the example.

For this example, the fermentation broth was prepared using 50 g/l of starch hydrolyzate, 6.25 g/l of corn steep liquor and 4 g/l of corn gluten. Sodium acetate was added to the medium to give the acetate equivalent of an acetic acid concentration of 5 g/l . Fermentations were conducted in sealed serum vials of 160 ml capacity. Into each vial was placed 10 ml of the fermentation medium and 10 ml of inoculum. The headspace gas in the vials was made up of CO (0.1 atm), $N_2$ (0.8 atm), $CO_2$ (0.05 atm) and $H_2$ (0.05 atm). A control was run which initially contained 0.9 atm $N_2$, 0.05 atm $CO_2$, 0.05 atm $H_2$, and no CO in the headspace. The initial pH of the fermentation broth was 5.45 and the flasks were shaken at 200 revolutions per minute at 35±1° C. for 48 hours. At the end of the fermentation, the gases were carefully released from the vials and collected over acidified brine. The gas volume was measured and its composition was determined by gas chromatography. The liquid was analyzed for organic acids and solvents by high-performance liquid chromatography. Carbohydrate in the liquid was measured as dextrose using a YSI glucose analyzer (available from the Yellow Springs Instrument Company of Yellow Springs, Ohio) after a sample of the mixture had been hydrolyzed with glucoamylase. Results of the example and the control given in Table I show that the uptake of organic acids and the production of butanol (BuOH) and ethanol (EtOH) is enhanced and that the production of hydrogen and acetone is decreased when carbon monoxide is present in the fermentation vials.

TABLE I

| Headspace CO (atm) | Carbohydrate Conc. (g/l as Dextrose) | | Acids (g/l) | | | | Solvents (g/l) | | | $H_2$ Produced (g/l) |
|---|---|---|---|---|---|---|---|---|---|---|
| | | | Acetic | | Butyric | | Acetone | BuOH | EtOH | |
| | 0 hr | 48 hr | 0 hr | 48 hr | 0 hr | 48 hr | 48 hr | 48 hr | 48 hr | |
| Example | | | | | | | | | | |
| 0.1 | 47.3 | 1.8 | 4.3 | 3.2 | 1.8 | 0.4 | 4.3 | 12.8 | 2.5 | 0.62 |
| Control | | | | | | | | | | |
| 0 | 47.3 | 0.7 | 4.8 | 4.0 | 1.5 | 1.8 | 6.2 | 11.7 | 0.9 | 1.0 |

EXAMPLE 2

The general procedure of Example 1 was followed except that no sodium acetate was added to the fermentation medium. As a consequence, no acetic acid was present at the start of the fermentation. Each fermentation vial contained 20 ml of fermentation medium and 2 ml of inoculum. Sufficient butyric acid was added to give an initial butyric acid concentration of 4.4 g/l and the fermentations were run for 72 hours. The results given in Table II show that the uptake of butyric acid and the production of butanol and ethanol is enhanced and the production of acetone is decreased when carbon monoxide is present in the fermentation vials.

TABLE II

| Headspace CO (atm) | Carbohydrate Conc. (g/l as Dextrose) | | Acids (g/l) | | | | Solvents (g/l) | | |
|---|---|---|---|---|---|---|---|---|---|
| | | | Acetic | | Butyric | | Acetone | BuOH | EtOH |
| | 0 hr | 72 hr | 0 hr | 72 hr | 0 hr | 72 hr | 72 hr | 72 hr | 72 hr |
| Example | | | | | | | | | |
| 0.1 | 53.0 | 1.2 | 0 | 2.9 | 4.4 | 0.9 | 4.1 | 14.0 | 1.4 |
| Control | | | | | | | | | |
| 0 | 53.0 | 1.0 | 0 | 2.4 | 4.4 | 2.3 | 5.5 | 12.4 | 0.7 |

EXAMPLE 3

The general procedure of Example 2 was followed except that the fermentation vials contained 30 ml of medium and 3 ml of inoculum. In this experiment, the fermentation gases were released every 24 hours and a calculated amount of carbon monoxide was injected to maintain the carbon monoxide partial pressure at 0.1 atm. In a second experiment the carbon monoxide partial pressure was increased to 0.15 atm after 24 hours and returned to this partial pressure by another addition of carbon monoxide after 48 hours. Analyses of the starting materials and final products after 72 hours for these two examples and for a control to which no carbon monoxide was added are given in Table III. These results show the increased production of butanol and ethanol and the reduced production of acetone in the presence of carbon monoxide.

TABLE III

| Headspace CO (atm) | Carbohydrate Conc. (g/l as Dextrose) | | Butyric Acid (g/l) | | Solvents (g/l) | | | Butanol[a] Yield |
|---|---|---|---|---|---|---|---|---|
| | | | | | Acetone | BuOH | EtOH | |
| | 0 hr | 72 hr | 0 hr | 72 hr | 72 hr | 72 hr | 72 hr | |
| Examples | | | | | | | | |
| 0.1 (0–72 hr) | 51.4 | 0.4 | 4.8 | 1.0 | 3.8 | 14.7 | 1.6 | 0.27 |
| 0.1 (0–24 hr) 0.15 (24–72 hr) | 51.4 | 0.3 | 4.8 | 0.6 | 2.9 | 15.0 | 2.0 | 0.27 |
| Control | | | | | | | | |
| 0 | 51.4 | 0.3 | 4.8 | 1.4 | 5.1 | 13.3 | 0.8 | 0.24 |

[a]Butanol Yield = $\dfrac{\text{g Butanol Produced}}{\text{g Carbohydrate Consumed + g Butyric Acid Consumed}}$

EXAMPLE 4

The general procedure of Example 1 was followed using higher initial concentrations of carbohydrate in the fermentation medium. The fermentation medium consisted of approximately 90 g/l of 10 D.E. starch hydrolyzate, 12.5 g/l corn steep liquor to which was added 7 g/l of butyric acid. The inoculum was prepared by growing cells for 18 hours in 100 ml of the fermentation medium in a 125-ml Erlenmeyer seed flask. For the fermentations, 3 ml of the seed inoculum was added to 30 ml of the fermentation medium and the fermentation was conducted at 34° C. The fermentation gases were vented at 24-hour intervals and a calculated amount of carbon monoxide was added to maintain its partial pressure at 0.1 atm. After 76 hours, the fermentations had stopped. The fermentation broths were then analyzed for residual carbohydrates, solvents, and acids. Control runs were made in which no carbon monoxide was added to the headspace. The results given in Table IV show that increased amounts of butyric acid are converted to solvents in the presence of carbon monoxide. Further, larger amounts of butanol and ethanol were produced in the presence of carbon monoxide even though more carbohydrate was consumed in the control experiments. The amount of acetone produced was also much less in the fermentations run in the presence of carbon monoxide.

TABLE IV

| Headspace CO (atm) | Carbohydrate Conc. (g/l as Dextrose) | | Butyric Acid (g/l) | | Solvents g/l | | | Butanol[a] Yield |
|---|---|---|---|---|---|---|---|---|
| | 0 hr | 76 hr | 0 hr | 76 hr | Acetone 76 hr | BuOH 76 hr | EtOH 76 hr | |
| Examples | | | | | | | | |
| 0.1 | 86.6 | 33.0 | 7.0 | 2.0 | 3.7 | 16.3 | 0.9 | 0.28 |
| 0.1 | 86.6 | 32.3 | 7.0 | 2.2 | 3.8 | 15.9 | 0.8 | 0.27 |
| Controls | | | | | | | | |
| 0 | 89.5 | 26.7 | 7.0 | 5.2 | 6.8 | 14.1 | 0.4 | 0.22 |
| 0 | 89.5 | 27.1 | 7.0 | 5.2 | 6.7 | 14.2 | 0.4 | 0.22 |

[a] Butanol Yield = $\dfrac{\text{g Butanol Produced}}{\text{g Carbohydrate Consumed + g Butyric Acid Consumed}}$

EXAMPLE 5

To 1 liter of a culture medium containing 60 g of 10 D.E. starch hydrolyzate, 7.5 g of corn steep liquor and 5 g of corn gluten in a 2-liter stirred fermentor was added 100 ml of inoculum prepared as in Example 1. A 50-ml portion of the inoculated medium was removed and allowed to ferment in a sealed serum vial which contained no CO to serve as a control. The fermentor was stirred at a rate of 200 rpm while the liquid was sparged at the rate of 100 ml/min with a gas containing by volume percentages 20% CO, 30% $H_2$, 48% $N_2$ and 2% $CO_2$. The fermentation was conducted at 35° C.

Initially, the fermentor sparged with CO began to produce lactic acid, butanol and ethanol. During this phase, the pH was controlled at about 5 by the addition of 4N NaOH. After 50 hours, about 30% of the carbohydrate had been consumed and the lactic acid reached a peak concentration of 6 g/l. The fermentation then began to consume lactic acid and produce increased amounts of butanol and ethanol. At this stage, the pH was allowed to rise to about 6 and was controlled at this value by the addition of 4N HCl. After 100 hours, the concentration of lactic acid had fallen to below 1 g/l. The fermentation was stopped after 190 hours when 94% of the carbohydrate had been consumed. No acetone was produced during the entire fermentation. The control which contained no carbon monoxide in the headspace gave no evidence of producing an appreciable amount of lactic acid and produced acetone to a concentration of 4.8 g/l. This experiment demonstrates that when the fermentation with C. acetobutylicum is conducted in the presence of CO at a partial pressure of 0.2 atm or higher, there is no production of acetone. It also shows that the fermentation can be made to produce a fairly high concentration of lactic acid which is metabolized upon further fermentation.

Thus, it is apparent that there has been provided, in accordance with the invention, an improved fermentation process for the production of butanol which reduces the formation of the by-products, acetone and hydrogen. While the invention has been described in conjunction with specific embodiments thereof, it is evident that many alternatives, modifications, and variations will be apparent to those skilled in the art in light of the foregoing description. Accordingly, it is intended to include all such alternatives, modifications, and variations as set forth within the spirit and scope of the appended claims.

What is claimed is:

1. A process for the production of butanol comprising fermenting carbohydrates in an aqueous medium at suitable conditions of temperature and pH with *Clostridium acetobutylicum* in the presence of a gas containing carbon monoxide at a partial pressure of from about 0.05 atm to about 0.3 atm, and recovering said butanol.

2. The process of claim 1 wherein the fermentation is carried out at a temperature of from about 34° C. to about 40° C.

3. The process of claim 1 wherein the fermentation is carried out at a pH of from about 4.5 to about 6.5.

4. The process of claim 1 wherein the carbohydrates comprise a starch hydrolyzate of from about 5 D.E. to about 20 D.E.

5. The process of claim 1 wherein the aqueous medium further comprises acetic acid.

6. The process of claim 1 wherein the fermentation reaction medium is sparged with a carbon monoxide-containing gas.

7. The process of claim 1 wherein the *Clostridium acetobutylicum* is strain ATCC 39236.

8. The process of claim 1 wherein said aqueous medium further comprises butyric acid.

9. The process of claim 8 wherein the fermentation is carried out at a temperature of from about 34° C. to about 40° C.

10. The process of claim 8 wherein the fermentation is carried out at a pH of from about 4.5 to about 6.5.

11. The process of claim 8 wherein the fermentation reaction medium is sparged with a carbon monoxide-containing gas.

12. The process of claim 8 wherein the *Clostridium acetobutylicum* is strain ATCC 39236.

* * * * *